US012508410B2

(12) United States Patent
Hoffer

(10) Patent No.: US 12,508,410 B2
(45) Date of Patent: Dec. 30, 2025

(54) MOLDABLE GRIPPING DEVICE AND METHOD OF USE

(71) Applicant: David Hoffer, Fountain Valley, CA (US)

(72) Inventor: David Hoffer, Fountain Valley, CA (US)

( * ) Notice: Subject to any disclaimer, the term of this patent is extended or adjusted under 35 U.S.C. 154(b) by 117 days.

(21) Appl. No.: 18/391,932

(22) Filed: Dec. 21, 2023

(65) Prior Publication Data

US 2025/0205465 A1 Jun. 26, 2025

(51) Int. Cl.
*A61M 37/00* (2006.01)

(52) U.S. Cl.
CPC ............................... *A61M 37/0076* (2013.01)

(58) Field of Classification Search
None
See application file for complete search history.

(56) References Cited

U.S. PATENT DOCUMENTS

| | | | |
|---|---|---|---|
| 5,155,878 A | 10/1992 | Dellis | |
| 9,487,656 B2 | 11/2016 | Iijima | |
| 10,697,730 B2 | 6/2020 | Brown | |
| D928,315 S | 8/2021 | Morrison | |
| D972,131 S | 12/2022 | Chen | |
| 2009/0007387 A1 | 1/2009 | Laghi | |
| 2010/0206138 A1 | 8/2010 | Clark | |
| 2014/0025099 A1 | 1/2014 | Morrison | |
| 2024/0157105 A1 * | 5/2024 | Barry | A61M 39/24 |

FOREIGN PATENT DOCUMENTS

| | | | |
|---|---|---|---|
| JP | 2010047643 A * | 3/2010 | A47G 21/00 |
| WO | WO2016011991 | 1/2016 | |

OTHER PUBLICATIONS

Fukuda JP2010047643A 2010 English Translation (Year: 2010).*

* cited by examiner

*Primary Examiner* — Jacob T Minskey
*Assistant Examiner* — Adrien J Bernard

(57) ABSTRACT

A moldable gripping device for use with a tattoo machine includes a tube and a Room Temperature Vulcanization (RTV) silicone rubber. The tube has a first end, a second end, and an outer surface. A tattoo machine can be inserted into the tube so that the tube is removably secured to the tattoo machine with an operable end of the tattoo machine protruding from the first end of the tube. The RTV silicone rubber comprises a first part and a second part, which are mixable to form a substrate. The substrate is moldable to the outer surface of the tube, deformable by grasping in a hand of a user, and curable to form a custom molded grip. The custom molded grip is substantially nonpliable and is molded to fit the hand of the user.

19 Claims, 7 Drawing Sheets

MOLDABLE GRIPPING DEVICE AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to grips and more particularly pertains to a new custom grip for use with a tattoo machine. Tattooing entails repetitive motion which can cause strain to hands of users and can lead to carpal tunnel syndrome. An easy to prepare and inexpensive grip that could be used once and discarded would be highly advantageous to tattoo artists.

(2) Description of Related Art Including Information Disclosed Under 37 CFR 1.97 and 1.98

The prior art relates to grips for handheld devices, in particular tattoo machines. The prior art discloses moldable handgrips for handguns utilizing a thermoplastic and moldable inner layer in combination with a resilient outer layer. The prior art also discloses moderately customizable grips for tattoo tubes that are not moldable.

BRIEF SUMMARY OF THE INVENTION

An embodiment of the disclosure meets the needs presented above by generally comprising a tube and a Room Temperature Vulcanization (RTV) silicone rubber. The tube has a first end, a second end, and an outer surface. The tube is configured for selective insertion of a tattoo machine such that the tube is removably secured to the tattoo machine with an operable end of the tattoo machine protruding from the first end of the tube. The RTV silicone rubber comprises a first part and a second part, which are mixable to form a substrate. The substrate is moldable to the outer surface of the tube, deformable by grasping in a hand of a user, and curable to form a custom molded grip. The custom molded grip is substantially nonpliable and is molded to fit the hand of the user.

Another embodiment of the disclosure includes a method of preparing a custom molded grip for use with a tattoo machine. The method entails provision of a moldable gripping device, according to the disclosure above. Steps of the method include mixing the first part and the second part of the RTV silicone rubber to form the substrate, molding the substrate to the outer surface of the tube, deforming the substrate by grasping in a hand of a user, allowing the substrate to cure to form a custom molded grip, and inserting a tattoo machine into the tube.

Yet another embodiment of the disclosure includes a custom molded grip preparation kit, which comprises a tube and a Room Temperature Vulcanization (RTV) silicone rubber, according to the disclosure above. The first part and the second part of the RTV silicone rubber are individually packaged in respective amounts sufficient to generate a quantity of the substrate sufficient to be moldable to the outer surface of the tube, deformable by grasping in a hand of a user, and curable to form a custom molded grip.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
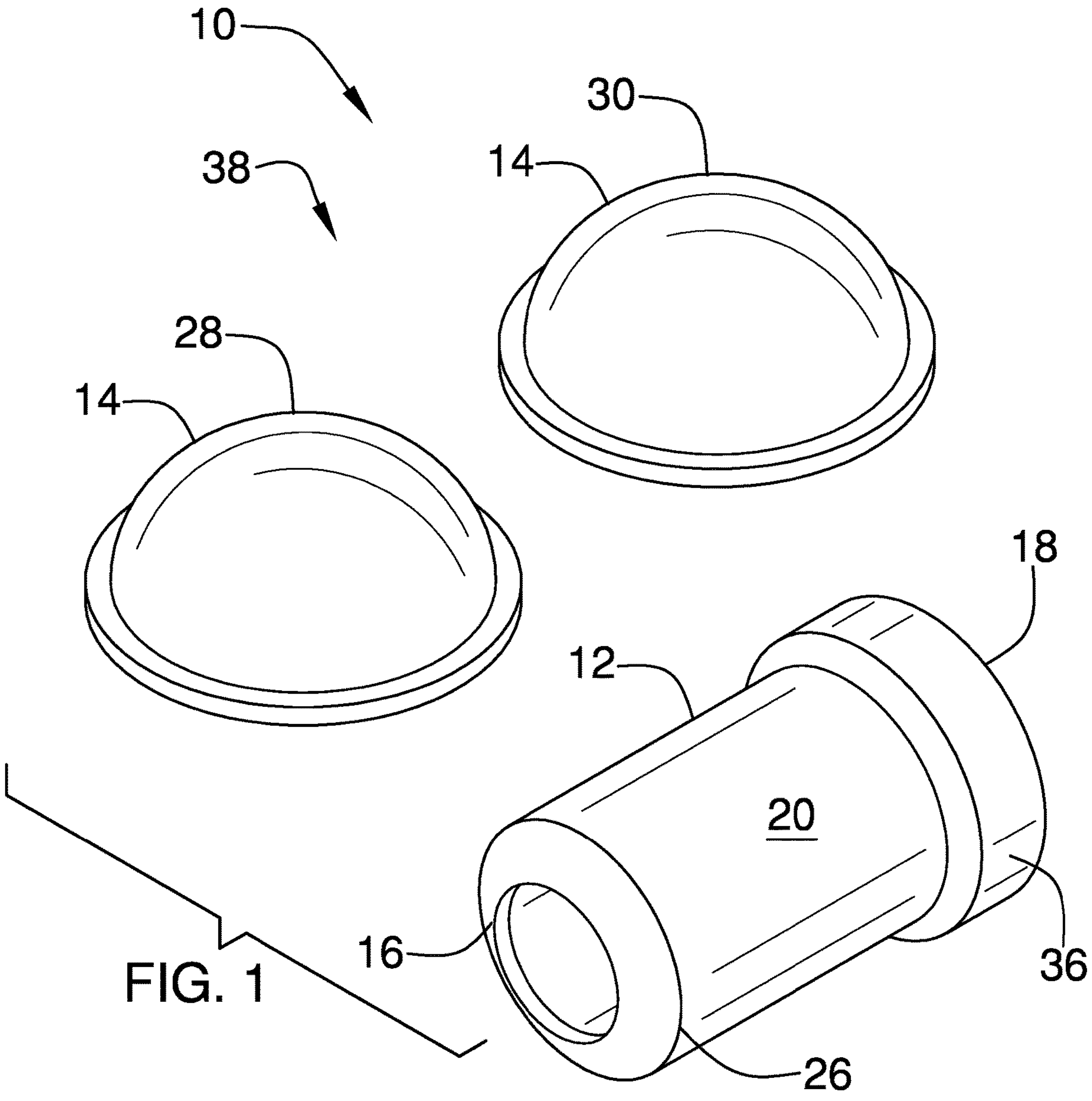
FIG. 1 is a kit view of a moldable gripping device according to an embodiment of the disclosure.
Figure 2:
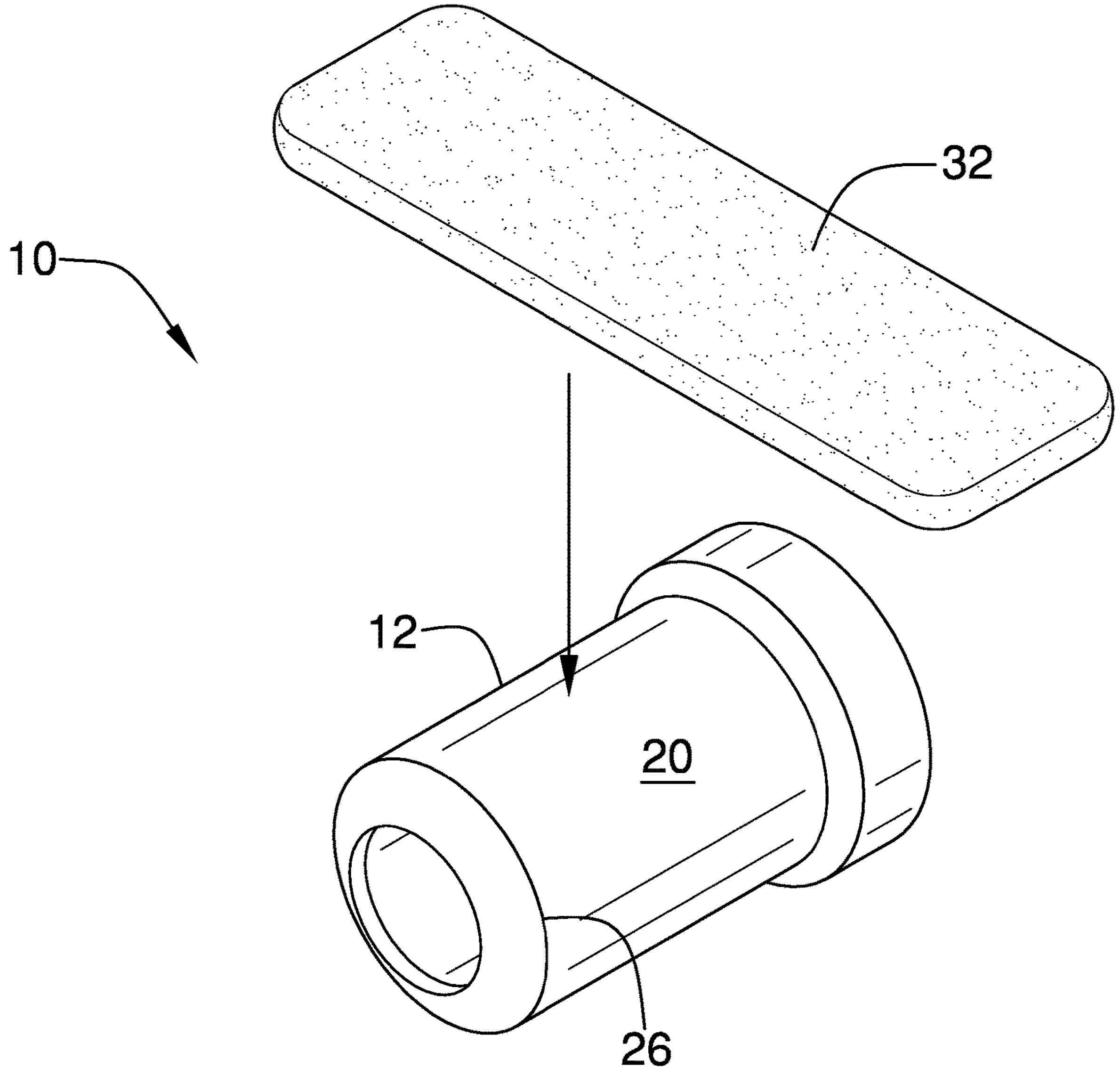
FIG. 2 is an in-use view of an embodiment of the disclosure.

With reference now to the drawings, and in particular to FIGS. 1 through 8 thereof, a new custom grip embodying the principles and concepts of an embodiment of the disclosure and generally designated by the reference numeral 10 will be described.

Figure 5:
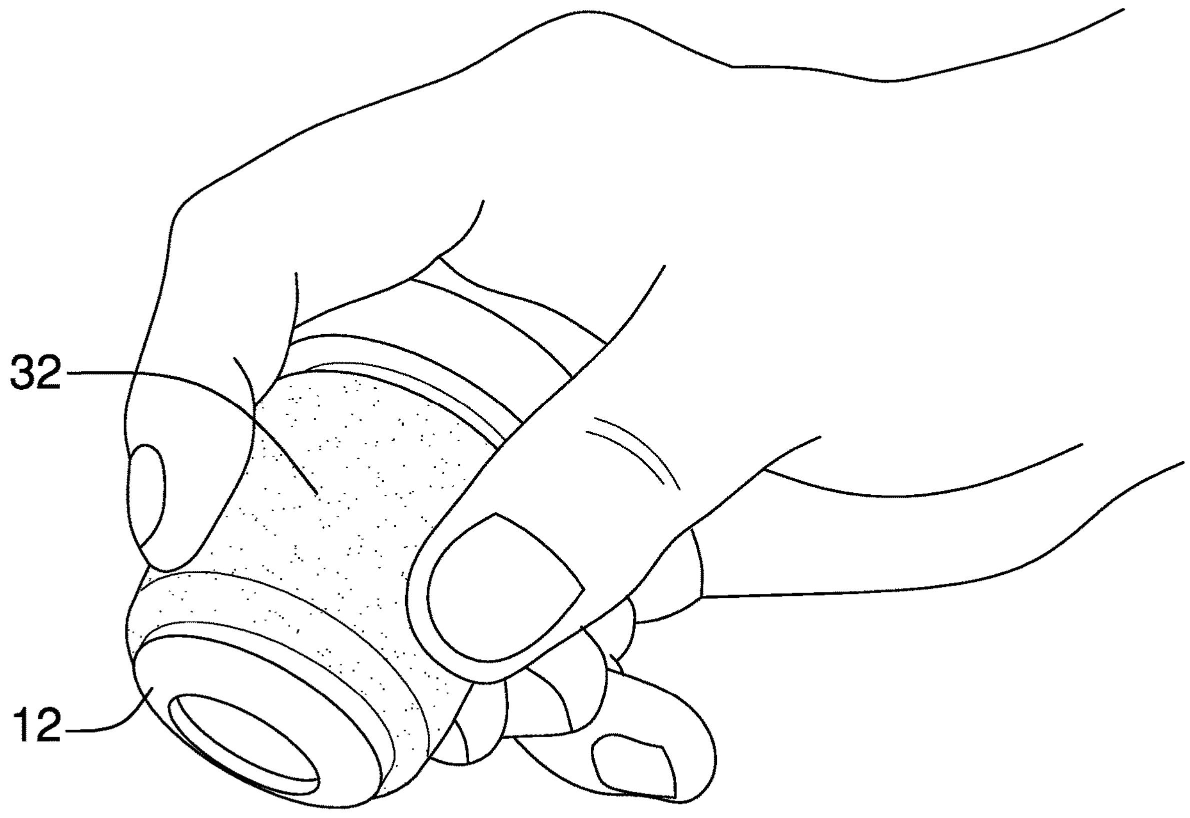
FIG. 5 is an in-use view of an embodiment of the disclosure.
Figure 6:
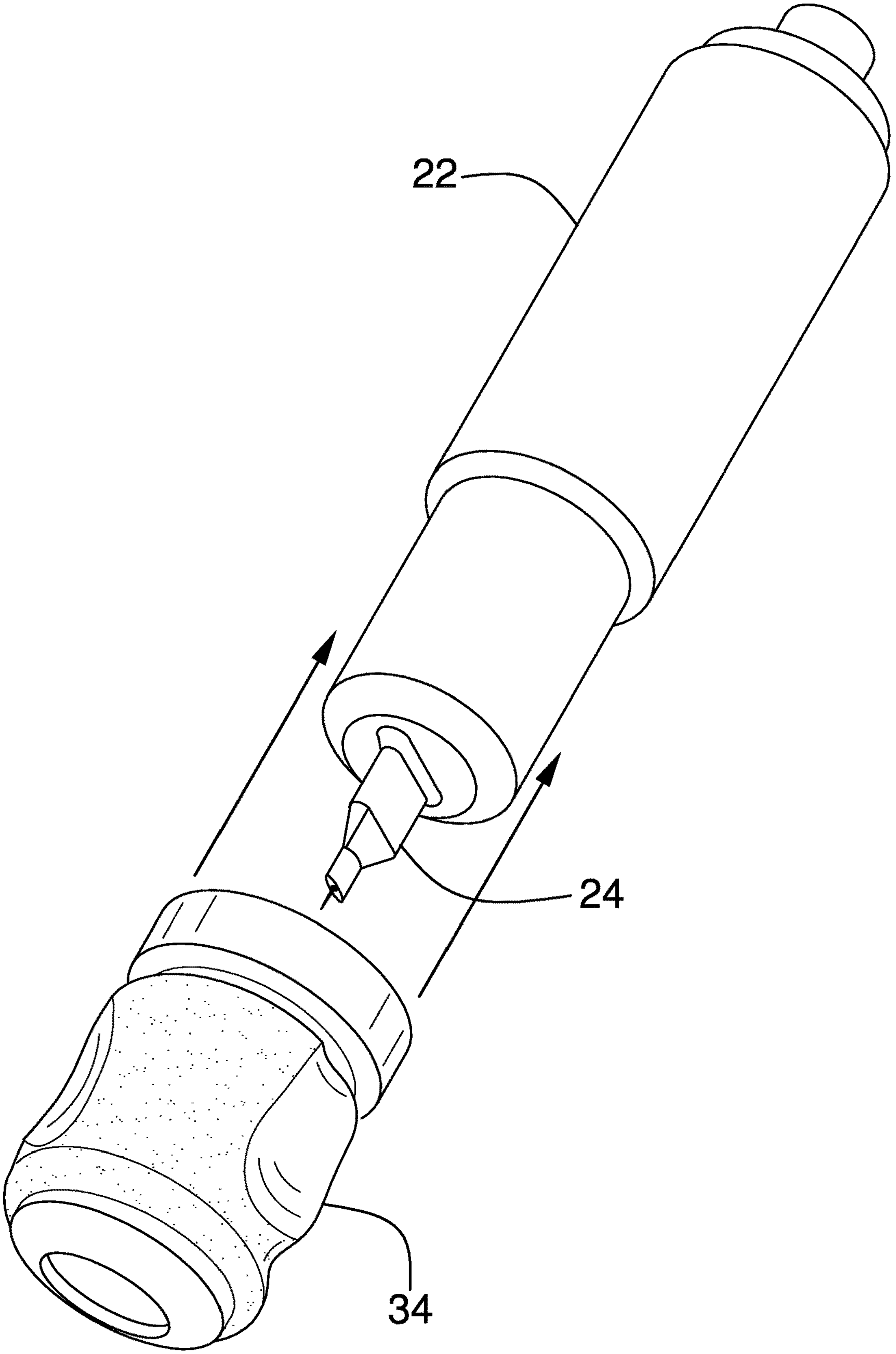
FIG. 6 is an in-use view of an embodiment of the disclosure.
Figure 7:
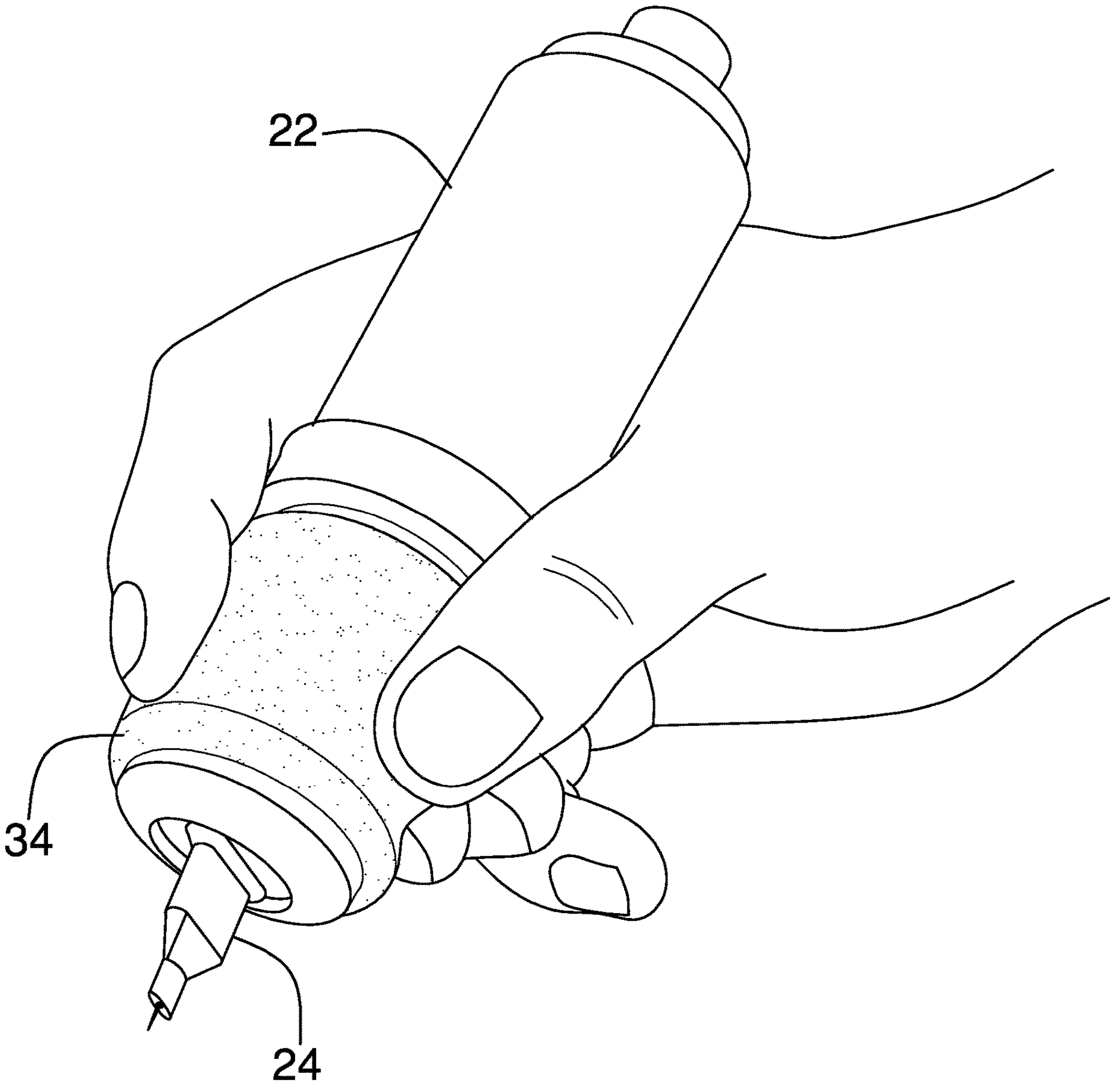
FIG. 7 is an in-use view of an embodiment of the disclosure.
Figure 8:
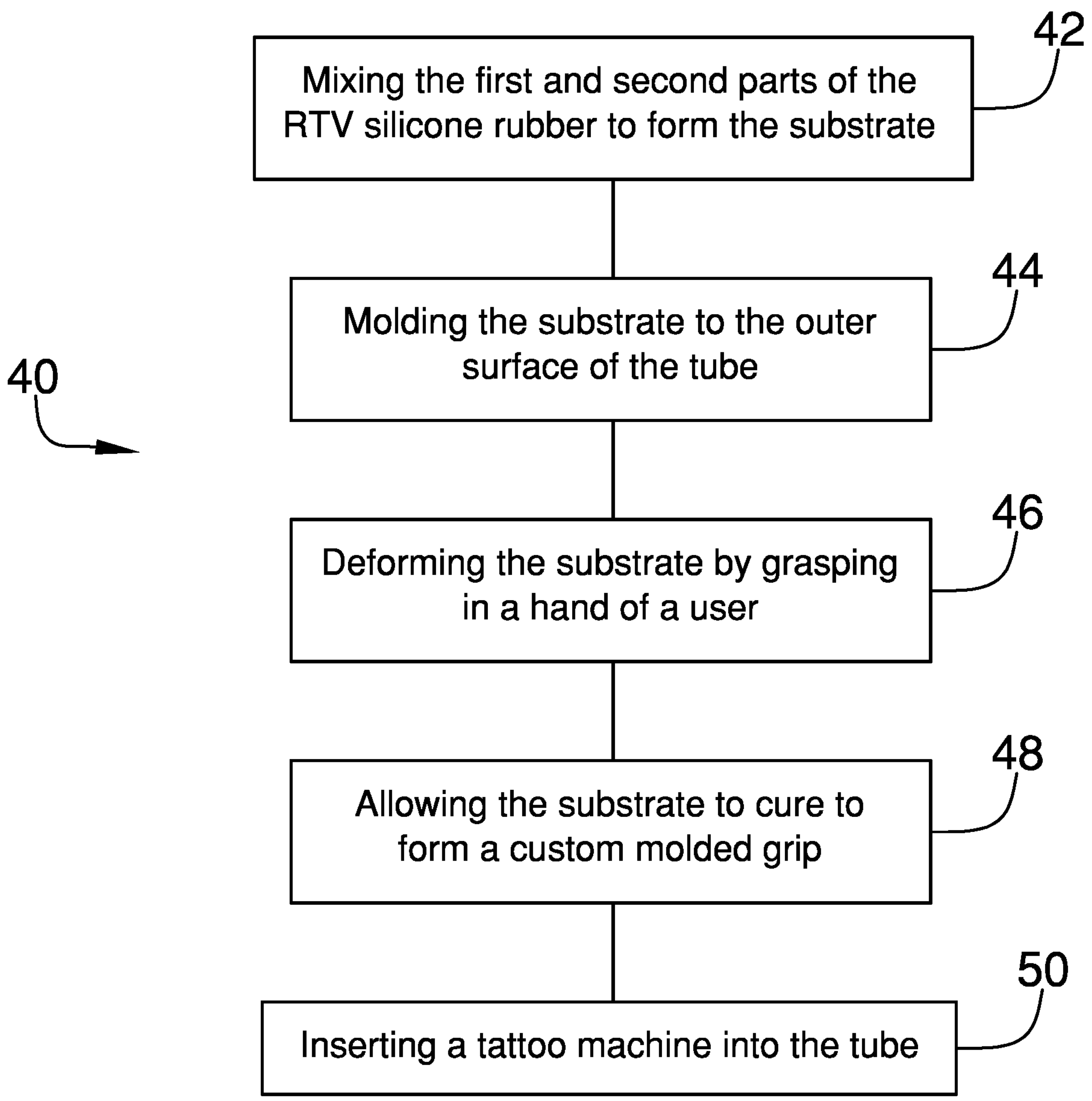
FIG. 8 is a flow diagram for a method utilizing an embodiment of the disclosure.

As best illustrated in FIGS. 1 through 8, the moldable gripping device 10 generally comprises a tube 12 and a Room Temperature Vulcanization (RTV) silicone rubber 14, as is shown in FIG. 1. The tube 12 has a first end 16, a second end 18, and an outer surface 20. The tube 12 is configured for selective insertion of a tattoo machine 22 such that the tube 12 is removably secured to the tattoo machine 22 with an operable end 24 of the tattoo machine 22 protruding from the first end 16 of the tube 12, as is shown in FIG. 7. The tube 12 has a cross-sectional profile 26, which typically would be circular but which also could be alternatively shaped, such as, but not limited to, rectangular, triangular, oval, or the like, so that the tube 12 can be removably secured to tattoo machines 22 having a variety of shapes.

Figure 3:
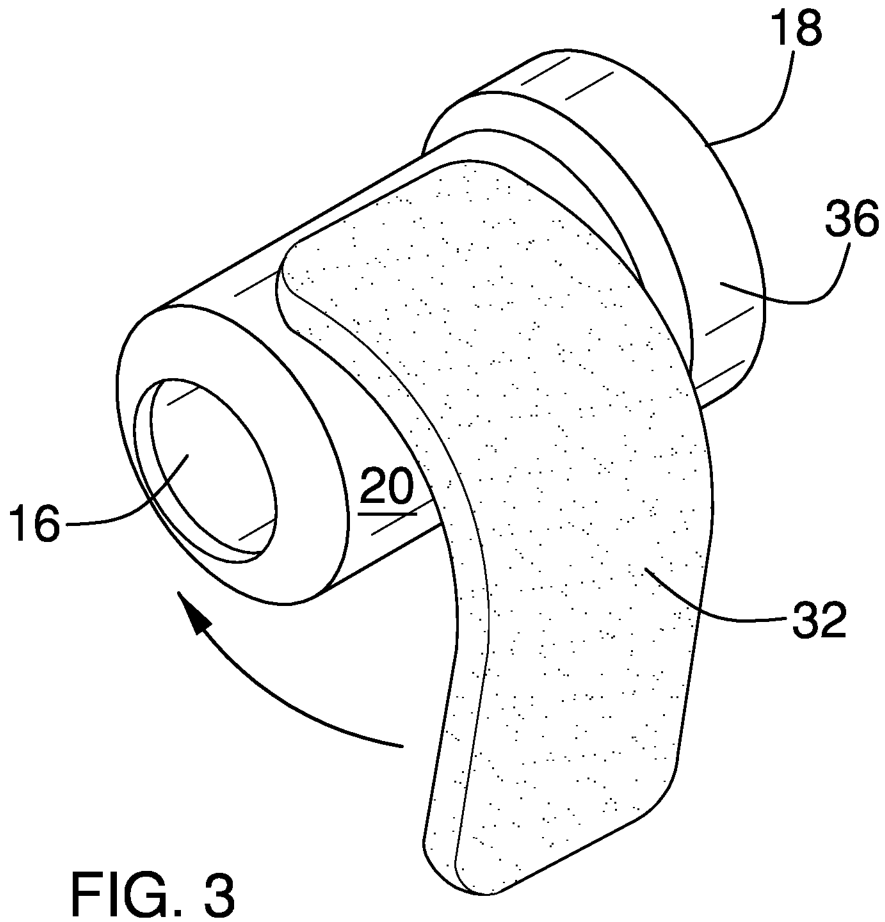
FIG. 3 is an in-use view of an embodiment of the disclosure.
Figure 4:
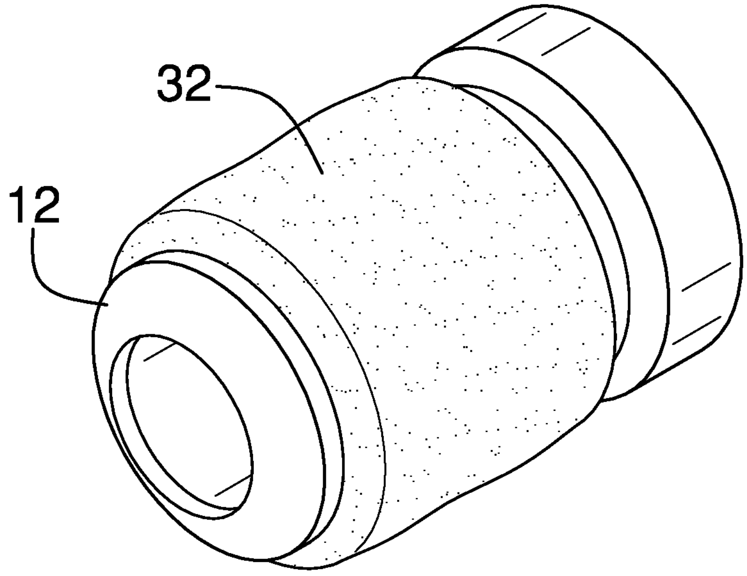
FIG. 4 is an in-use view of an embodiment of the disclosure.

The RTV silicone rubber 14 comprises a first part 28 and a second part 30, which are mixable to form a substrate 32. The substrate 32 is moldable to the outer surface 20 of the tube 12, as is shown in FIGS. 3 and 4, deformable by grasping in a hand of a user, as is shown in FIG. 5, and then curable to form a custom molded grip 34, as is shown in FIG. 6. The custom molded grip 34 is substantially nonpliable and is molded to fit the hand of the user. Two part silicone rubber systems are well known in the prior art and are available from numerous suppliers.

The RTV silicone rubber 14 has a working time of from 2.0 to 8.0 minutes and a curing time of from 1.0 to 8.0 minutes. The RTV silicone rubber 14 may have a working time of from 3.0 to 5.0 minutes and a curing time of from 2.0 to 4.0 minutes. The first part 28 and the second part 30 are anticipated to be mixable in a ratio that is substantially 1:1, although the present invention anticipates other mixing ratios depending on the particular two part silicone rubber system being utilized.

As is shown in the figures, a ring 36 is attached to and extends circumferentially around the tube 12 adjacent to the second end 18. The ring 36 functions to preclude the substrate 32 from entering the second end 18 of the tube 12 during molding.

The custom molded grip 34 is intended to be single use to facilitate sterile tattooing practices. As the custom molded grip 34 is specifically customized to the user, it provides improved ergonomics and limits stain to the hand of the user and potential of developing or exacerbating carpal tunnel syndrome, which can be caused by the repetitive motions involved in tattooing. Another advantage of using a custom molded grip 34 is a firmer and surer grip, thus limiting a likelihood of inadvertent ink injection.

Also anticipated by the present invention is a custom molded grip preparation kit 38, which comprises a tube 12 and a Room Temperature Vulcanization (RTV) silicone rubber 14. The tube 12 has a first end 16, a second end 18, and an outer surface 20. The tube 12 is configured for selective insertion of a tattoo machine 22 such that the tube 12 is removably secured to the tattoo machine 22 with an operable end 24 of the tattoo machine 22 protruding from the first end 16 of the tube 12. The RTV silicone rubber 14 comprises a first part 28 and a second part 30, which are mixable to form a substrate 32. The first part 28 and the second part 30 are individually packaged in respective amounts sufficient to generate a quantity of the substrate 32 sufficient to be moldable to the outer surface 20 of the tube 12, deformable by grasping in a hand of a user, and curable to form a custom molded grip 34. The custom molded grip 34 is substantially nonpliable and molded to fit the hand of the user.

In use, the moldable gripping device 10 enables a method of preparing a custom molded grip for use with a tattoo machine 40. The method 40 entails provision of a moldable gripping device 10, according to the specification above. A first step 42 of the method 40 is mixing the first part 28 and the second part 30 of the RTV silicone rubber 14 to form the substrate 32. A second step 44 of the method 40 is molding the substrate 32 to the outer surface 20 of the tube 12. A third step 46 of the method 40 is deforming the substrate 32 by grasping in a hand of a user. A fourth step 48 of the method 40 is allowing the substrate 32 to cure to form a custom molded grip 34. A fifth step 50 of the method 40 is inserting a tattoo machine 22 into the tube 12 so that an operable end 24 of the tattoo machine 22 protrudes from the first end 16 of the tube 12 and such that the tube 12 and the custom molded grip 34 are removably secured to the tattoo machine 22.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A moldable tattoo machine gripping device comprising:

a tattoo machine;

a tube, the tube having a first end, a second end, and an outer surface, the tattoo machine being insertable into the tube such that the tube is removably secured to the tattoo machine with an operable end of the tattoo machine protruding from the first end of the tube; and a Room Temperature Vulcanization (RTV) silicone rubber comprising a first part and a second part, the first part and the second part being mixable to form a substrate, the substrate being moldable to the outer surface of the tube, deformable by grasping in a hand of a user, and curable to form a custom molded grip, the custom molded grip being substantially nonpliable and molded to fit the hand of the user.

2. The moldable tattoo machine gripping device of claim 1, further including a ring attached to and extending circumferentially around the tube adjacent to the second end to preclude the substrate from entering the second end of the tube during molding.

3. The moldable tattoo machine gripping device of claim 1, wherein the tube has a cross-sectional profile, the cross-sectional profile being circular.

4. The moldable tattoo machine gripping device of claim 1, wherein the RTV silicone rubber has a working time of from 2.0 to 8.0 minutes and a curing time of from 1.0 to 8.0 minutes.

5. The moldable tattoo machine gripping device of claim 4, wherein the RTV silicone rubber has a working time of from 3.0 to 5.0 minutes and a curing time of from 2.0 to 4.0 minutes.

6. The moldable tattoo machine gripping device of claim 1, wherein the first part and the second part are mixable in a ratio that is substantially 1:1.

7. The moldable tattoo machine gripping device of claim 1, further including:

the tube having a cross-sectional profile, the cross-sectional profile being circular;

the RTV silicone rubber having a working time of from 3.0 to 5.0 minutes and a curing time of from 2.0 to 4.0 minutes;

the first part and the second part being mixable in a ratio that is substantially 1:1; and a ring being attached to and extending circumferentially around the tube adjacent to the second end to preclude the substrate from entering the second end of the tube during molding.

8. A method of preparing a custom molded grip for use with a tattoo machine, the method comprising providing a moldable gripping device according to claim 1, and:

mixing the first part and the second part of the RTV silicone rubber to form the substrate;

molding the substrate to the outer surface of the tube;

deforming the substrate by grasping in a hand of a user;

allowing the substrate to cure to form a custom molded grip; and inserting a tattoo machine into the tube, such that an operable end of the tattoo machine protrudes from the first end of the tube and such that the tube and the custom molded grip are removably secured to the tattoo machine.

9. The method of claim 8, further including a ring attached to and extending circumferentially around the tube adjacent to the second end to preclude the substrate from entering the second end of the tube during molding.

10. The method of claim 8, wherein the tube has a cross-sectional profile, the cross-sectional profile being circular.

11. The method of claim 8, wherein the RTV silicone rubber has a working time of from 2.0 to 8.0 minutes and a curing time of from 1.0 to 8.0 minutes.

12. The method of claim 11, wherein the RTV silicone rubber has a working time of from 3.0 to 5.0 minutes and a curing time of from 2.0 to 4.0 minutes.

13. The method of claim 8, wherein the first part and the second part are mixable in a ratio that is substantially 1:1.

14. A custom molded tattoo machine grip preparation kit comprising:

a tattoo machine;

a tube, the tube having a first end, a second end, and an outer surface, the tattoo machine being insertable into the tube such that the tube is removably secured to the tattoo machine with an operable end of the tattoo machine protruding from the first end of the tube; and a Room Temperature Vulcanization (RTV) silicone rubber comprising a first part and a second part, the first part and the second part being mixable to form a substrate, the first part and the second part being individually packaged in respective amounts sufficient to generate a quantity of the substrate sufficient to be moldable to the outer surface of the tube, deformable by grasping in a hand of a user, and curable to form a custom molded grip, the custom molded grip being substantially non-pliable and molded to fit the hand of the user.

15. The custom molded tattoo machine grip preparation kit of claim 14, further including a ring attached to and extending circumferentially around the tube adjacent to the second end to preclude the substrate from entering the second end of the tube during molding.

16. The custom molded tattoo machine grip preparation kit of claim 14, wherein the tube has a cross-sectional profile, the cross-sectional profile being circular.

17. The custom molded tattoo machine grip preparation kit of claim 14, wherein the RTV silicone rubber has a working time of from 2.0 to 8.0 minutes and a curing time of from 1.0 to 8.0 minutes.

18. The custom molded tattoo machine grip preparation kit of claim 17, wherein the RTV silicone rubber has a working time of from 3.0 to 5.0 minutes and a curing time of from 2.0 to 4.0 minutes.

19. The custom molded tattoo machine grip preparation kit of claim 14, wherein the first part and the second part are mixable in a ratio that is substantially 1:1.

* * * * *